United States Patent [19]

Schulz et al.

[11] Patent Number: 4,843,171

[45] Date of Patent: Jun. 27, 1989

[54] 1,1-DIALKOXY-2-METHYL-4,4-DIACYLOXY-2-BUTENES

[75] Inventors: Bernhard Schulz, Schwertzingen; Rolf Fischer, Heidelberg, both of Fed. Rep. of Germany

[73] Assignee: BASF Aktiengesellschaft, Ludwigshafen, Fed. Rep. of Germany

[21] Appl. No.: 68,442

[22] Filed: Jul. 1, 1987

[30] Foreign Application Priority Data

Jul. 5, 1986 [DE] Fed. Rep. of Germany ....... 3622601

[51] Int. Cl.⁴ .............................................. C07C 67/02
[52] U.S. Cl. ........................................ 560/262; 560/1; 560/112; 560/121; 560/122; 549/375; 549/454
[58] Field of Search ........................ 560/262, 112–122; 549/375, 454

[56] References Cited

U.S. PATENT DOCUMENTS 3,639,437 2/1972 Fischer et al. ...................... 560/262
4,410,719 10/1983 Fischer et al. ...................... 560/262

FOREIGN PATENT DOCUMENTS 3244272 5/1984 Fed. Rep. of Germany ...... 560/262

Primary Examiner—Paul J. Killos
Attorney, Agent, or Firm—Rupert B. Hurley, Jr.

[57] ABSTRACT

1,1-Dialkoxy-2-methyl-4,4-diacyloxy-2-butenes having the general structure:

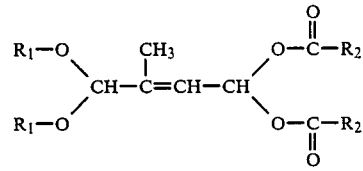

in which $R_1$ represents alkyl substituents having from 1 to 5 carbon atoms, or both $R_1$ substituents together represent a single ethylene or propylene substituent, or a single $C_1$–$C_2$ alkyl substituent, and $R_2$ represents alkyl substituents having from 1 to 5 carbon atoms, or cycloalkyl substituent having from 5 to 7 carbon atoms, or aromatic substituents (preferably phenyl substituents). These new compounds are useful as building blocks in the synthesis of terpenes and carotenoids.

4 Claims, No Drawings

1,1-DIALKOXY-2-METHYL-4,4-DIACYLOXY-2-BUTENES

The present invention pertains to 1,1-dialkoxy-2-methyl-4,4-diacyloxy-2-butenes having the general structure I:

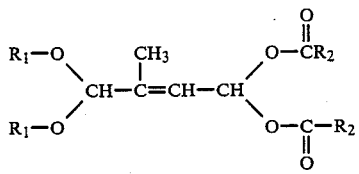

in which $R_1$ substituents are selected from the group consisting of alkyl substituents having 1 to 5 carbons and an alkylene bridge having from 1 to 3 carbon atoms. If the $R_1$ substituents are an alkylene bridge having 2 to 3 carbon atoms (i.e. ethylene or propylene), either a 5 or a 6 member ring is formed, respectively. The ethylene or propylene bridge may itself be substituted with a $C_1$ to $C_4$ substituent, preferably an alkyl substituent. Preferably the $R_1$ substituents are selected from the group consisting of alkyl substituents having from 1 to 3 carbon atoms, an ethylene bridge, and a 2,2-dimethylpropylene bridge, and the $R_2$ substituents are alkyl substituents having from 1 to 3 carbon atoms. Also, preferably both $R_1$ substituents are together a 2,2-dimethyl propylene bridge.

$R_2$ stands for an alkyl substituent having from 1 to 5 carbon atoms, preferably from 1 to 3 carbon atoms, a cycloalkyl radical having from 5 to 7 carbon atoms, or an aromatic substituent (preferably a phenyl substituent).

The new compounds are useful $C_5$ building blocks for the synthesis of terpenes and carotenoids. These compounds can be prepared by the process disclosed in European Patent Application EP No. 68 372, (hereby incorporated by reference) by using 2-methyl-4,4-diacyloxy-2-butenals having the general formula II:

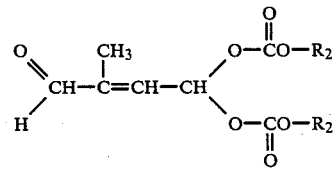

As an example, the preparation of (I) can be carried out by reacting (II) with alkanols and/or alkanediols, or by reacting (II) with ortho-formic esters. Houben-Weil, *Methoden de Organischen Chemie*, 4th edition, volume 6/3, page 222, describes this process. Furthermore, it is known that catalysts must be present during the formation of acetals of aldehydes and ketones with ortho esters. On page 224 of the Heuben Weil reference it is pointed out that the reaction of $\alpha,\beta$-unsaturated aldehydes with ortho esters must be carried out either in the complete absence of an alcohol or with only small quantities of alcohol present. Otherwise, addition of the alcohol to the double bond would result.

Also described in volume 6/3 of Houben-Weyl, (supra), page 224, is the formation of acetals of crotonaldehyde. Here it is taught that in order to achieve good yields, a reaction time of several days is required in the presence of a catalyst and in the absence of an alcohol. Therefore, one cannot expect ready formation of the acetal of 2-methyl-4,4-diacyloxy-2-butenol (II), in a good yield, without having the double bonds or the acyl functions (known as relatively unstable) attacked by the alcohol (solvent). This effect is furthered here since molecule (II) contains a double bond which is conjugated with respect to the aldehyde.

In the novel compounds having formula (I), the following substituents are of particular interest:
where
$R_1$ is: methyl, ethyl, or propyl; where both $R_1$ substituents together are an: ethylene, propylene, or 2,2-dimethylpropylene bridge; and
where
$R_2$ is: methyl, propyl, cyclohexyl, or phenyl.

The resulting compounds are advantageously used in coupling carbon-carbon double bonds through reactions of carbonyl compounds with phosphorylides (i.e. the Wittig reaction) used as $C_5$ building blocks. Their significance for preparing terpenes and carotenoids lies primarily in the fact that the acyl groups in (I) are saponified into aldehyde groups when carrying out the Wittig reaction under the reaction conditions, while the acetal groups are not attacked under basic conditions of the Wittig reaction. Using the 3-methyl-4,4-dialkoxy-2-butenals resulting here in situ, the substituents are able to be introduced selectively into the newly forming olefin in the reaction with phosphorylides:

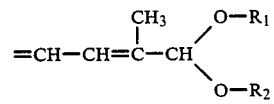

Therefore it is possible to react a triphenylphosphonium salt, obtained from vitamin A, with 1,1-dimethoxy-2-methyl-4,4-diacetoxy-2-butene in the presence of methanol, water, and magnesium hydroxide, resulting in a good yield of the corresponding $C_{25}$-dimethylacetal.

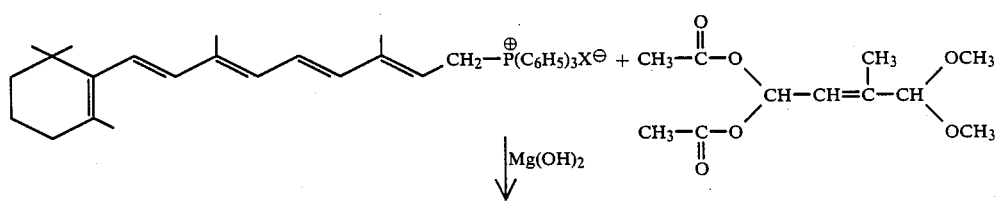

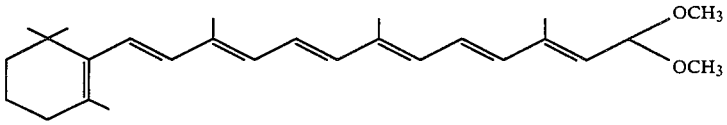

The novel 1,1-dialkoxy-2-methyl-4,4-diacyloxy-2-butenes (I) possess an advantage when used as terpene building units, in that no separate hydrolysis step is required for the cleavage of the acyl-protective groups. In contrast to the acetal-protective groups which are only removable under acidic conditions, the saponification of the acyl groups results under the conditions of the Wittig reaction.

EXAMPLE 1

Preparation and Characterization of 1,1-dimethoxyl-2-methyl-4,4-diacetoxy-2-butene A solution was made by combining 25 grams of 2-methyl-4,4-diacetoxy-2-butenal and 20 grams of o-formic trimethylester in 95 ml methanol. The solution was stirred for 23 hours at 40° C. The methanol, formic methylester, and unreacted o-formic trimethylester were distilled off in a rotary condenser. From the remaining material, 23.6 grams of 1,1-dimethoxy-2-methyl-4,4-diacetoxy-2-butene (84 percent E-isomer, 16 percent Z-isomer) was obtained via fractional distillation. The butene had a boiling point of from 92° C. to 94° C. at 0.3 bar. The butene yield was 77 percent relative to the 2-methyl-4,4-diacetoxy-2-butenal used.

Both the E-butene (prepared above) and the Z-butene were characterized via NMR analysis, (using deuterochloroform as a solvent and tetramethylsilane as an internal standard), as follows:

E-1,1-dimethoxy-2-methyl-4,4-diacetoxy-2-butene.

$\delta = 1.80$ (d, I=1 Hz, 3H), 2.09 (S, 6H), 3.29 (S,6H), 4.53 (S, 1H), 5.70 (d width, I=8 Hz, 1H), 7.40 (d, I=8 Hz, 1H).

Z-1,1-dimethoxy-2-methyl-4,4-diacetoxy-2-butene.

$\delta = 1.75$ (d, I=1 Hz, 3H), 2.09 (S,6H), 3.35 (S, 6H), 5.08 (S, 1H), 5.49 (d width, I =8 Hz, 1H), 7.55 (d, I=8 Hz, 1H).

EXAMPLE 2

Preparation and Characterization of 1,1-[2′,2′-dimethyl-propylene-1′,3′-dioxy]-2-methyl-4,4-diacetoxy-2-butene 2-Methyl-4,4-diacetoxy-2-butenal was reacted with neopentyl glycol, in the presence of p-toluene sulfonic acid, so that 1,1-[2′,2′-dimethyl-propylene-1′,3′-dioxyl]-2-methyl-4,4-diacetoxy-2-butene was obtained. The butene obtained had a boiling point of 126° C.-130° C. (at a pressure of 0.8 bar). This butene was then characterized via NMR analysis ($n^2\beta = 1.4608$; 1H-NMR-spectra; solvent was CDCl$_3$, TMS was the internal standard):

$\delta = 0.74$ (s,3H), 1.20 (s, 3H), 1.86 (d, 3H), 2.08 (s, 6H), 3.55 (m, 4H), 4.68 (s, 1H), 5.72 (d, J =ca. 8 Hz, 1H), 7.41 (d, J =ca. 8 Hz, 1H).

EXAMPLE 3

Preparation of β-apo-12′-carotenal

A 200 ml aliquot of 60 percent methanol/40 percent water was placed in a 1 liter, 3-neck flask along with 23.4 grams (0.4 mol) of magnesium hydroxide. While the resulting solution was being stirred at room temperature, 31.8 grams of 93 percent 1,1-dimethoxyl-4,4-diacetoxy-2-butene were added. Then 200 ml of axerophtyltriphenylphosphonium hydrogensulfate in methanol was added dropwise, over a 30 minute period. [The axerophtyltriphenylphosphonium hydrogensulfate had been prepared from 32.8 grams of Vitamin A-acetate.] The reaction mixture was stirred an additional 5 hours at 50° C. Afterwards, 500 ml heptane, 400 ml of 20 percent sulfuric acid, and 400 ml of methanol were added and then stirred for 30 minutes at 50° C. The lower phase was separated and discarded, following which the upper phase was washed three times with 250 ml of 60 percent methanol. The upper phase was concentrated, and 31.0 grams of a yellow-red oil ($E_1^1 = 1680$, max. 410 nm) was obtained. The yield was about 89 percent of the crude β-apo-12′-carotenal. This crude product was then converted into β-apo-8′-carotenal.

EXAMPLE 4

Preparation of β-apo-8′-carotenal

31 Grams of the crude β-apo-12′-carotenal prepared in Example 3 was dissolved in 80 ml of heptane. Then, while stirring this solution, 35 ml of a 30 percent sodium methylate solution (in methanol) and 110 ml of solution of 47 grams (0.11 moles) of 4,4-dimethoxy-3-methyl-2-butenyltriphenylphosphonium chloride (in methanol) were added to the solution. The temperature was then increased to 45° C. Afterwards it was refluxed for one hour. Then the solution was treated with 120 ml of heptane followed by 100 ml of water at 50° C. The solution was then washed twice with 250 ml of 60 percent methanol. After evaporation of methanol, 40 grams of crude β-apo-8′-carotenal-dimethylacetal was obtained. This acetal was then dissolved in 50 ml heptane and 250 ml isopropanol, and was then treated with 20 ml of 32 percent sulfuric acid, and was then stirred for 12 hours at room temperature. The resulting crystalline material was suction filtered and washed several times with cold methanol. 22.4 Grams of pure β-apo-8′-carotenal was produced ($E_1^1 = 2540$, λ max.=459 nm, in cyclohexane). The yield was 60.8 percent of the theoretical yield.

EXAMPLE 5

The process described in Example 1 was again carried out, except that 1,1-[2′,2′-Dimethylpropylene-1′,3′-dioxy]-2-methyl-4,4-diacetoxy-2-butene was used in place of 1,1′-dimethoxy-2-methyl-4,4-diacetoxy-2-butene. The process resulted in a 52 percent yield of crude β-apo-12′-carotenal. From this crude, crystalline pure β-apo-8′-carotenal was produced in a 57 percent yield.

Experiments 1 through 5 were not optimized. The crystalline β-apo-8′-carotenals exhibited all of the characteristics (with respect to UV-spectra NMR and C-13 NMR) reported in the literature for β-apo-8′-carotenal.

The embodiments of the invention in which an exclusive property or privilege is claimed are defined as follows:

1. A compound having the formula:

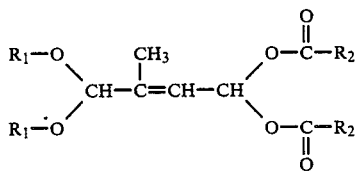

in which the $R_1$ substituents are selected from the group consisting of alkyl substituents having from 1 to 5 carbon atoms, an alkylene bridge having from 2 to 3 carbon atoms, the alkylene bridge being unsubstituted or substituted with a $C_1$ to $C_4$ alkyl group, and a 2,2-dimethyl-propylene bridge, and the $R_2$ substituents are selected from the group consisting of alkyl substituents having from 1 to 5 carbon atoms, cyclo alkyl substituents having from 5 to 7 carbon atoms, and phenyl substituents.

2. A compound as described in claim 1 in which the $R_1$ substituents are selected from the group consisting of alkyl substituents having from 1 to 3 carbon atoms, an ethylene bridge, and a 2,2-dimethyl propylene bridge, and the $R_2$ substituents are alkyl substituents having from 1 to 3 carbon atoms.

3. A compound as described in claim 1 wherein the ethylene or propylene bridge is itself substituted with a $C_1$ to $C_4$ alkyl substituent.

4. A compound as described in claim 2 wherein $R_1$ is a methyl substituent and $R_2$ is a methyl substituent.

* * * * *